United States Patent [19]

Radola et al.

[11] Patent Number: 5,672,416

[45] Date of Patent: *Sep. 30, 1997

[54] FABRIC FOR THE PREPARATION OF ELECTROPHORESIS GELS

[75] Inventors: Bertold Radola, Munich; Horst Schwall, Gau-Algesheim; Manfred Demharter, Heidelberg, all of Germany

[73] Assignee: Serva Feinbiochemica GmbH & Co., Heidelberg, Germany

[*] Notice: The terminal 44 months of this patent has been disclaimed.

[21] Appl. No.: 391,591

[22] PCT Filed: Oct. 21, 1988

[86] PCT No.: PCT/EP88/00946

§ 371 Date: Aug. 21, 1989

§ 102(e) Date: Aug. 21, 1989

[87] PCT Pub. No.: WO89/03721

PCT Pub. Date: May 5, 1989

[30] Foreign Application Priority Data

Oct. 24, 1987 [DE] Germany .................. 37 36 087.6

[51] Int. Cl.[6] .................................................. B32B 07/00
[52] U.S. Cl. ................... 428/247; 428/252; 428/253; 428/286
[58] Field of Search .................... 428/247, 252, 428/253, 286

[56] References Cited

U.S. PATENT DOCUMENTS

| 3,875,044 | 4/1975 | Renn et al. ................................ 204/299 |
| 4,006,069 | 2/1977 | Hiratsuka et al. ................... 204/180 G |
| 4,116,743 | 9/1978 | Davis ........................................ 156/333 |
| 4,415,428 | 11/1983 | Nochumson et al. ............... 204/299 R |
| 4,452,892 | 6/1984 | Rosevear .................................. 435/176 |
| 4,483,885 | 11/1984 | Chait et al. ............................... 427/58 |
| 4,650,551 | 3/1987 | Carl et al. ............................... 204/59 R |
| 4,985,128 | 1/1991 | Ebersole et al. ..................... 204/182.8 |

FOREIGN PATENT DOCUMENTS

| 968516 | 6/1975 | Canada . |
| 3032069 | 3/1982 | Germany . |
| 60164242 | 8/1985 | Japan . |
| 962575 | 7/1964 | United Kingdom . |

OTHER PUBLICATIONS

*Fabric Reinforced Polyacrylamide Gels For Electroblotting* —H. Nishizawa et al., Electrophoresis vol. 6, pp. 349–350 (1985).

Primary Examiner—Helen Lee
Attorney, Agent, or Firm—R. P. Raymond; M-E. M. Devlin; A. R. Stempel

[57] ABSTRACT

The invention relates to new fabrics with improved properties for the preparation of electrophoresis gels.

10 Claims, No Drawings

FABRIC FOR THE PREPARATION OF ELECTROPHORESIS GELS

The invention relates to new fabrics with improved properties for the preparation of electrophoresis gels and processes for producing them.

Polyacrylamide gels and agarose are used in numerous electrophoresis techniques as anticonvective and screening matrices. The gels are used in two forms:
1) cylindrical gels, which were very popular for some time, are nowadays particularly preferred for first-dimension separation in two-dimensional electrophoresis; and
2) Flat gels, which are used in the techniques most frequently practised nowadays, namely sodium dodecylsulphate (SDS) electrophoresis and isoelectric focussing.

A fact common to both configurations is that during the separation the gels are supported from the outside, e.g. by the walls of a glass test tube or a sheet of glass. After separation the gels are evaluated, e.g. by protein staining, enzyme visualisation or blotting. The unsupported gels are subjected to considerable mechanical stress, which means that gels with a layer thickness of less than 0.7 mm cannot be used.

A further considerable disadvantage is that conventional gels are not dimensionally stable and will readily change their dimensions by swelling or shrinkage in solvents of different composition, making it difficult or impossible to evaluate the components visualised.

By polymerising the gels onto suitably pretreated polyester films it is possible to overcome to some extent the disadvantages described above. Using suitably pretreated polyester films it is possible to prepare ultrathin gels, i.e. those with a thickness of about 50–350 microns, which have crucial practical advantages over gels of conventional thickness (e.g. 1 to 3 mm) in isoelectric focussing and SDS electrophoresis. However, film-supported gels of this kind have the disadvantage that they are not optimal for capillary blotting and are completely unsuitable for electroblotting.

An alternative to the externally stabilised gels are fabric-supported gels with internal stabilisation. Such gels are open on both sides and are therefore particularly suitable for blotting. However, they are also of interest for other applications, e.g. preparative isoelectric focussing. Contrary to expectations, however, it has been found that such electrophoresis gels prepared on fabrics do not meet the practical requirements.

Hitherto, it has been assumed that because of the greater contact surface between the fabric and the gel, as compared with gels on support films, the fabric-supported gels will adhere adequately even to non-pretreated fabrics. This may be true for those applications in which the fabric-supported gels are merely stained after electrophoretic separation, since no very great demands are made of the gel adhesion in such cases. However, the situation is different in the application of fabric-supported gels which is currently of most importance, namely blotting. In this technique, after separation from the gel using suitable membranes, e.g. nitrocellulose membranes, a blot is produced in which the separated components are immobilised so that they are then available for further reactions, e.g. immunological detection methods. The transfer of the separated components into the membrane requires good contact between the surface of the gel and the nitrocellulose membrane since otherwise some of the resolution achieved in the gel will be lost.

The transfer may be carried out either by capillary blotting or by electroblotting in an electrical field. In both transfer techniques, pressure is applied to the gel and the membrane in order to obtain as accurate a copy as possible in the blot.

For further evaluation of the blot the membrane must be lifted away from the surface of the gel. It has been found, unexpectedly, that the adhesion of the gels to the supporting fabric is inadequate. Parts of the gel or, in some cases, the entire surface of the gel is or are pulled away from the membrane as well, so that subsequent evaluation of the blot is impaired or even rendered completely impossible.

A further disadvantage of the fabric-supported gels used hitherto is that these gels frequently cannot be totally destained and consequently they have an uneven background. This may have a detrimental effect on further evaluation of the gels.

An object of this invention is therefore to provide industrial fabrics which make it possible to produce fabric-supported electrophoresis gels with improved properties, such as during evaluation.

We have found that the object may be achieved by using an industrial fabric which has a single or multilayer hydrophilic coating as an adhesion promoter.

Suitable fabrics are known from the prior art and are marketed by various companies. Industrial fabrics consisting of polyester with a defined mesh size of between 10 and 100 microns are preferred; fabrics of polypropylene or polyamide are also suitable. When choosing the fabric it should be ensured that it will not be damaged by the aggressive reagents or solvents frequently used in electrophoresis technology from time to time. Fabric-supported gels are preferably used for the preparation of ultrathin electrophoresis gels (50 to 500 microns), which means that the industrial fabrics used should have a thickness of between 40 and 70 microns, preferably 50 to 60 microns.

Adhesion promoters according to the invention include those compounds which are able to bring about cross-linking between the fabric and the gel which is subsequently to be applied. Suitable compounds are for example polymers and copolymers with reactive functional groups capable of crosslinking with the gel. German Offenlegungsschrift 30 32 069 discloses suitable copolymers based on maleic anhydride derivatives with unsaturated primary or secondary amines or epoxides containing C=C double bonds.

Copolymers of maleic anhydride and vinylalkylethers, copolymers of polysaccharides and allylglycidylethers and surfactants are also suitable.

Preferred adhesion promoters (crosslinking agents) include copolymers of maleic anhydride and vinylmethylether (e.g. Gantrez AN obtainable from Serva Technik GmbH of Heidelberg, Germany) with diallylamine; agarose and allylglycidylether (allylglycidyl agarose), or copolymers of maleic anhydride and methylvinylether (e.g. Gantrez AN), the preferred surfactant being Surfynol.

The coating according to the invention may consist of a single layer or may be made up of several layers. Multi-layer coatings may consist of combinations of individual layers which may contain different copolymers as adhesion promoters. If desired, a further coating of a surfactant such as 2,4,7,9-tetramethyl-5-decin-4,7-diol, may be applied to the mono- or multi-layered coating of crosslinking agent. In another embodiment the surfactant may be added directly to the adhesion promoter as a further component.

The composition and structure of the coating are most suitably adapted to the gel which is to be applied later.

The thickness of the coating is variable and may be adjusted, for example, during preparation by adjusting the viscosity of the solutions of adhesion promoter used during the immersion process. However, it is always necessary for the weave-like structure of the industrial fabric to be retained, i.e. the meshes of the fabric should not be closed up by the coating since otherwise the properties of the fabric supported gel will be adversely affected.

Fabrics according to the invention suitable for the preparation of a fabric supported polyacrylamide gel may, for example, have the following structure:,
- a) a polyester fabric with a pore size of between 50 and 100 microns, preferably 60 microns, and a thickness of between 40 and 70 microns.
- b) a 1st coating consisting of a copolymer of Gantrez and diallylamine,
- c) a 2nd coating of allylglycidyl agarose, and
- d) a 3rd coating of a surfactant e.g. Surfynol 104 (available from Serva Technik GmbH, Heidelberg, Germany)

Another fabric by way of example according to the invention for the preparation of a fabric supported agarose gel has a two-layer coating; e.g.
- a) a polyester fabric with a pore size of between 50 and 100 microns, preferably 60 microns,
- b) a 1st coating of Gantrez AN, and
- c) a 2nd coating of agarose.

Since the fabrics used are generally sold for other purposes (e.g. as screens), it may be advantageous to pretreat them in order to improve the adhesion of the coating. This may be done, for example, simply by washing them with water. The coatings may readily be prepared analogously to known immersion methods.

For this purpose, the copolymers or surfactants used are dissolved in suitable solvents, if possible volatile solvents. Suitable solvents include, for example, acetone, methanol, water and others, whilst care should be taken to ensure that the solvent does not damage the fabrics used. The fabrics are then dipped into the solution so that they are thoroughly wetted; the excess solution is then allowed to drip off and the now coated fabric is carefully dried. The fabric is preferably dried at elevated temperature. Additional coatings of the same or a different composition may subsequently be applied using the same process.

The fabrics thus prepared, once they have been carefully dried, may then be used to prepare fabric-supported electrophoresis gels. The corresponding techniques are known and need no further explanation.

The electrophoresis gels prepared from the fabrics according to the invention have considerable advantages over those prepared from conventional fabrics:

Fabric-supported gels prepared with fabric pretreated according to the invention have significantly better adhesion, which can be determined, for example, in a test using a dry membrane. Moistened membranes such as are used in blotting can readily be detached from the surface of the gel without tearing away even part of the gel.

A further advantage of the pretreated fabrics becomes apparent during manufacture of the fabric-supported gels. The strongly hydrophobic properties of the untreated fabric make it more difficult for the polymerisation solution to penetrate during preparation of ultrathin gels.

This disadvantage is substantially eliminated with the industrial fabrics treated according to the invention. The fabrics according to the invention make it possible to prepare ultrathin electrophoresis gels with thicknesses of between 50 and 500 microns, the preferred gels having a thickness of about 150 microns.

In addition to this advantage, the pretreated fabrics also show improved properties with regard to destaining and transfer efficiency. Whereas untreated fabrics often have an uneven background during destaining, the treated fabrics are practically uniformly destained. The transfer efficiency is also better with the treated fabrics. This ensures that the proteins are quantitatively transferred from the fabric to the membrane.

The following non-limiting examples illustrate embodiments of the invention:

EXAMPLE 1

Industrial Fabric for the Preparation of a Fabric Supported Polyacrylamide Electrophoresis Gel A fabric consisting of polyester (PES Monodur 60N, from Messrs. Verseidig, Kempen) is treated as follows.
- a) Preparation of the first coating layer: The fabric is immersed in a solution* of 6 liters of acetone, 381 mg of Gantrez AN 179 (Serva$^R$), 22 ml of DMF and 237.6 mg of diallylamine so that it is thoroughly wetted. Excess solution is then allowed to drip off and the fabric is dried at room temperature.

*The solution is only ready for use after 24 hours.
- b) Preparation of the second coating layer: The fabric treated as described in a) is dried and then immersed in a 0.2% solution of allylglycidyl agarose in water and then dried.
- c) Preparation of the third coating layer: After drying the fabric is finally immersed in a 0.1% ethanolic solution of Surfynol 104 (Serva$^R$) and dried.

The fabric thus prepared is then placed, in accordance with known methods, namely the so-called flap technique or cassette technique, in the monomer mixture of acrylamide and conventional additives (such as polymerisation initiator and other constituents, which then polymerises to form the gel.

EXAMPLE 2

Industrial Fabric for the Preparation of a Fabric Supported Agarose Electrophoresis Gel The polyester fabric (PES Monodur 60N) is prepared by the immersion method as described in Example 1.

| 1st coating | |
|---|---|
| Composition of the solution: | 8 liters of acetone |
|  | 8 g of Gantrez |
| 2nd coating | |
| Composition of the solution: | 8 g of agarose/5.6 ml water |
|  | 6 liters of methanol |
|  | 20 ml of glycerol |

The embodiments of the invention in which an exlusive property or privilege is claimed are defined as follows:

1. A fabric useful for the production of electrophoresis gels comprising a polyester fabric having a mesh size of between about 10 to about 100 μm, and also having a multilayer coating consisting of a first layer of a copolymer of maleic acid anhydride and vinylmethylether with diallylamine, a second layer of allylglycidyl agarose and a third layer of a surfactant.

2. A fabric useful for the production of electrophoresis gels comprising a polyester fabric having a mesh size of between about 10 to about 100 μm, and also having a two-layer coating consisting of a first layer of a copolymer of maleic acid anhydride and vinylmethylether and a second layer of agarose.

3. A fabric useful for the production of electrophoresis gels comprising a polyester fabric having a mesh size of between about 10 to about 100 μm and also having a coating, in at least two layers, of allylglycidyl agorose.

4. The fabric as recited in claim 3 wherein the outer layer of coating also comprises a surfactant.

5. A fabric-supported electrophoresis gel comprising a self-supporting polyester fabric having a mesh size of between about 10 to about 100 μm and a thickness of between about 40 to about 70 μm, the polyester fabric having a multilayer coating consisting of a first layer of a copolymer of maleic acid anhydride and vinylmethylether with diallylmine, a second layer of allylglycidyl agarose and a third layer of a surfactant, and an electrophoresis gel supported thereon.

6. A fabric-supported electrophoresis gel comprising a self-supporting polyester fabric having a mesh size of between about 10 to about 100 μm and a thickness of between about 40 to about 70 μm, the polyester fabric having a two-layer coating consisting of a first layer of a copolymer of maleic acid anhydride and vinylmethylether and a second layer of agarose, and an electrophoresis gel supported thereon.

7. A fabric-supported electrophoresis gel comprising a self-supporting polyester fabric having a mesh size of between about 10 to about 100 μm and a thickness of between about 40 to about 70 μm, the polyester fabric having a coating, in at least two layers, of allylglycidyl agarose, and an electrophoresis gel supported thereon.

8. The fabric-supported electrophoresis gel as recited in claim 7 wherein the outer layer of coating also comprises a surfactant.

9. The fabric-supported electrophoresis gel according to claim 5, the electrophoresis gel being polyacrylamide.

10. The fabric-supported electrophoresis gel according to claim 6, the electrophoresis gel being agarose.

* * * * *